US011734514B1

United States Patent
Shorter et al.

(10) Patent No.: US 11,734,514 B1
(45) **Date of Patent: *Aug. 22, 2023**

(54) AUTOMATED TRANSLATION OF SUBJECT MATTER SPECIFIC DOCUMENTS

(71) Applicant: IQVIA Inc., Danbury, CT (US)

(72) Inventors: Gary Shorter, Danbury, CT (US); Naouel Baili Ben Abdallah, Danbury, CT (US); Barry Ahrens, Danbury, CT (US)

(73) Assignee: IQVIA INC., Durham, NC (US)

( * ) Notice: Subject to any disclaimer, the term of this patent is extended or adjusted under 35 U.S.C. 154(b) by 340 days.

This patent is subject to a terminal disclaimer.

(21) Appl. No.: 17/098,812

(22) Filed: Nov. 16, 2020

Related U.S. Application Data

(63) Continuation of application No. 16/276,002, filed on Feb. 14, 2019, now Pat. No. 10,839,164.

(Continued)

(51) Int. Cl.
*G06F 40/00* (2020.01)
*G06F 40/30* (2020.01)
(Continued)

(52) U.S. Cl.
CPC ........... *G06F 40/30* (2020.01); *G06F 40/253* (2020.01); *G06F 40/284* (2020.01);
(Continued)

(58) Field of Classification Search
CPC ...... G06F 40/205; G06F 40/20; G06F 40/279; G06F 40/284; G06F 40/289;
(Continued)

(56) References Cited

U.S. PATENT DOCUMENTS

| | | | |
|---|---|---|---|
| 5,642,502 | A | 6/1997 | Driscoll |
| 6,625,599 | B1 | 9/2003 | Bera |

(Continued)

OTHER PUBLICATIONS

Tu, Z., Liu, Y., Shi, S., & Zhang, T. (2017). Learning to Remember Translation History with a Continuous Cache. Transactions of the Association for Computational Linguistics, 6, 407-420. (Year: 2017).*

*Primary Examiner* — Edgar X Guerra-Erazo
(74) *Attorney, Agent, or Firm* — John Maldjian; Stevens & Lee PC

(57) ABSTRACT

Documents in source natural languages are translated into target natural languages using a computer-implemented translation that is configured to operate within the domain of the subject matter of the documents that imposes specialized requirements for translation and readability. Subject matter specific documents typically include domain-specific terminology, are subject to various regulatory guidelines, and have different readability requirements depending on the intended reader. The computer-implemented translation applies machine-learning techniques that deconstruct elements of the subject matter specific document into a standard data structure and perform pre-processing steps to tokenize digitized document text to identify the correct sentence structure and syntax for the target natural language to optimize translation by, e.g., a neural machine translation engine. The text segments that are input into the neural machine translation engine are generated to be semantically meaningful in the target natural language to thereby enhance the understanding of the neural machine translation engine.

20 Claims, 14 Drawing Sheets

Related U.S. Application Data

(60) Provisional application No. 62/739,541, filed on Oct. 1, 2018.

(51) Int. Cl.
*G16H 10/20* (2018.01)
*G06N 3/04* (2023.01)
*G06F 40/295* (2020.01)
*G06F 40/253* (2020.01)
*G06F 40/284* (2020.01)
*G06N 3/08* (2023.01)

(52) U.S. Cl.
CPC ............. *G06F 40/295* (2020.01); *G06N 3/04* (2013.01); *G06N 3/08* (2013.01); *G16H 10/20* (2018.01)

(58) Field of Classification Search
CPC ........ G06F 40/295; G06F 40/30; G06F 40/35; G06F 40/40; G06F 40/47; G06F 40/45; G06F 40/44; G06F 40/42; G06F 40/51; G06F 40/55; G06F 40/56; G06F 40/58; G06F 40/263; G06F 40/268; G06F 40/237; G06F 40/242; G06F 40/253; G06F 40/216; G06F 40/10; G06N 20/00; G06N 20/10; G06N 20/20; G06N 3/04; G06N 3/0436; G06N 3/0427; G06N 3/0454; G06N 3/0445; G06N 3/08; G06N 5/048; G06N 5/04; G06N 7/00; G06N 7/02; G06N 7/023; G06N 7/026
See application file for complete search history.

(56) References Cited

U.S. PATENT DOCUMENTS

| | | | | |
|---|---|---|---|---|
| 7,024,351 | B2 | 4/2006 | Wang | |
| 7,321,861 | B1 | 1/2008 | Oon | |
| 7,379,946 | B2 | 5/2008 | Carus et al. | |
| 7,574,347 | B2 | 8/2009 | Wang | |
| 8,073,840 | B2 | 12/2011 | Smith et al. | |
| 8,180,783 | B1 | 5/2012 | Fletcher et al. | |
| 8,375,021 | B2 | 2/2013 | Sokolan et al. | |
| 8,407,165 | B2 | 3/2013 | Monroe et al. | |
| 8,768,723 | B2 | 7/2014 | Montyne et al. | |
| 9,286,061 | B2 | 3/2016 | Zhang et al. | |
| 9,905,229 | B2 | 2/2018 | Montyne et al. | |
| 10,607,042 | B1 * | 3/2020 | Dasgupta | G06F 40/253 |
| 10,803,250 | B2 * | 10/2020 | Chui | G06F 40/30 |
| 10,839,164 | B1 * | 11/2020 | Shorter | G06F 40/42 |
| 11,042,713 | B1 * | 6/2021 | Platt | G06N 5/01 |
| 2004/0024756 | A1 | 2/2004 | Rickard | |
| 2005/0050030 | A1 | 3/2005 | Gudbjartsson et al. | |
| 2006/0224579 | A1 | 10/2006 | Zheng | |
| 2009/0248442 | A1 | 10/2009 | Pacheco et al. | |
| 2010/0070448 | A1 | 3/2010 | Omogui | |
| 2011/0179074 | A1 | 7/2011 | Lee et al. | |
| 2011/0289035 | A1 | 11/2011 | Stojadinovic et al. | |
| 2012/0191716 | A1 | 7/2012 | Omoigui | |

* cited by examiner

100
Local processing
150
Remote processing
155
Neural machine translation engine
125
120
Remote service provider
Tokens in source natural language
140
Tokens in target natural language
145
Communications network
115
135
A P I
Computer-implemented translation tool
130
110
Local computing device
105
Human operator or translator Source natural language
205
Clinical trial documents
130
Computer-implemented translation tool
210
Document deconstruction
215
Natural language structuring pre-processing
220
Neural machine translation
225
Semantic ontology correction post-processing
230
Document reconstruction
Target natural language
235
Clinical trial documents
240
125
120
105
110

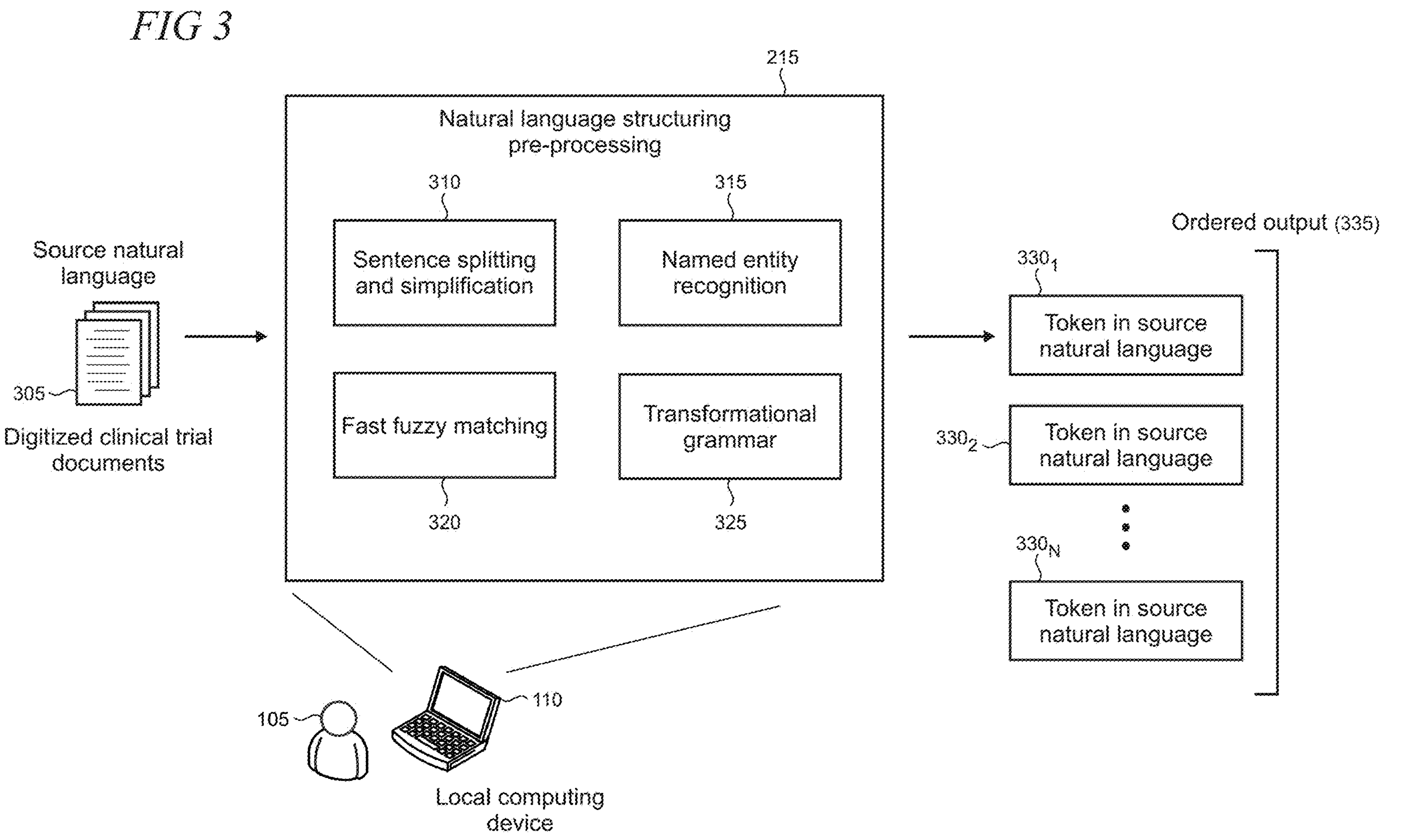
FIG 3
Source natural language
305
Digitized clinical trial documents
215
Natural language structuring pre-processing
310
Sentence splitting and simplification
315
Named entity recognition
Fast fuzzy matching
320
Transformational grammar
325
105
110
Local computing device
Ordered output (335)
$330_1$
Token in source natural language
$330_2$
Token in source natural language
$330_N$
Token in source natural language Ordered tokens
405
Ordered output (335)
$330_1$
Token in source natural language
$330_2$
Token in source natural language
$330_N$
Token in source natural language
135
API
125
Neural machine translation engine
135
API
225
Semantic ontology correction post-processing
410
Ordered translated tokens Clinical trial document text (510)
310
Sentence splitting and simplification
505
Cascade of finite-state transducers
Tokens (text segments with reduced complexity and length) (515)
520
Gazetteer list of abbreviations 315
Named entity recognition
605
Named entity recognition system
Clinical trial document text (610)
Exclude translation
620
Mask information
625
Extract information
630
615
Named entity table or database Clinical trial document text (710)
320
Fast fuzzy matching
705
Text matching system
Translated text in target natural language (715)
725
100%
0
Fuzzy match expression
720
Translation memory Transformational grammar
325
Clinical trial document text (810)
Transformation system
805
Tagger
835
Single represention for text having the same meaning (815)
Passive voice sentence transformation
820
Indirect sentence transformation
825
Word re-ordering transformation
830

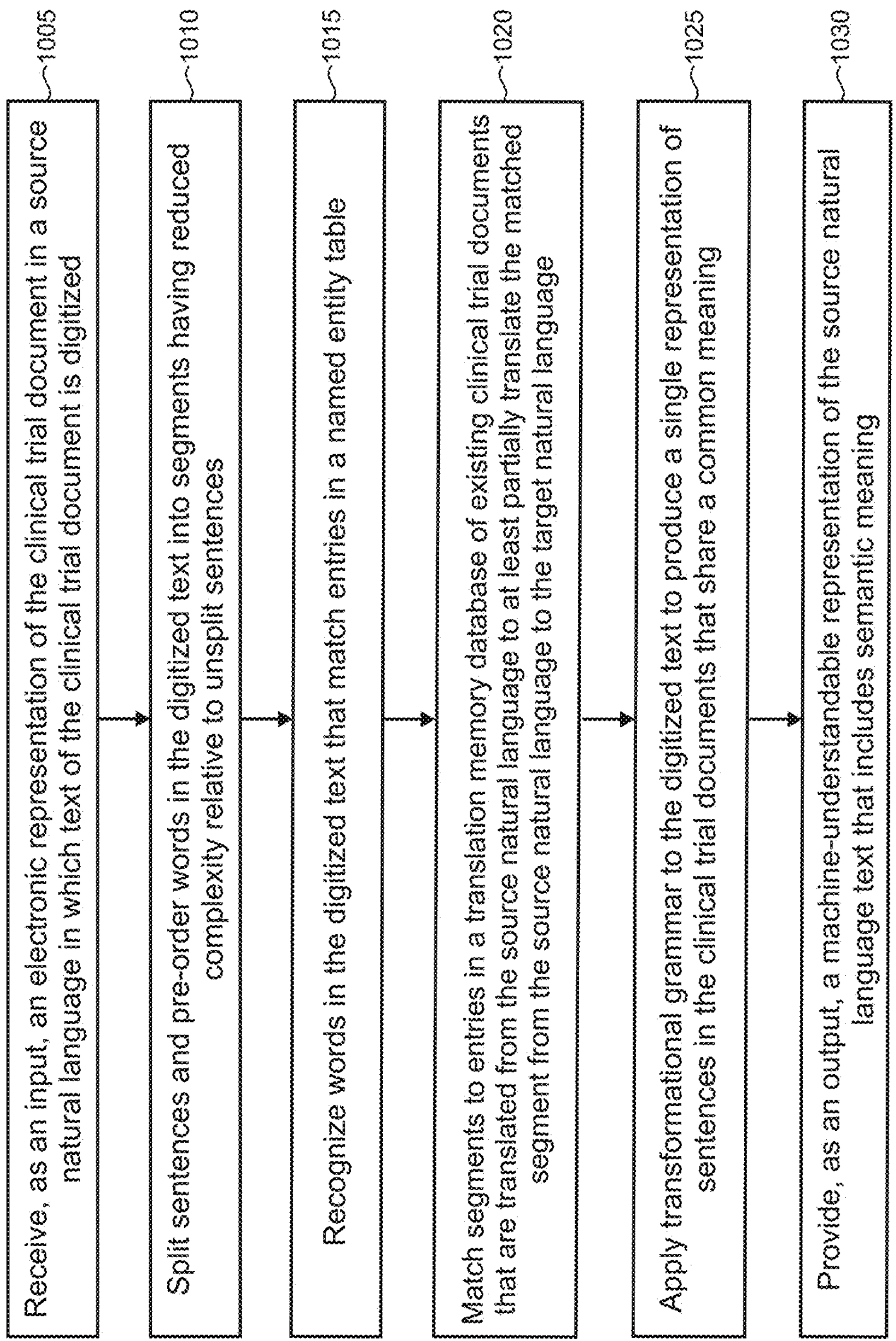
FIG 10
1000
Receive, as an input, an electronic representation of the clinical trial document in a source natural language in which text of the clinical trial document is digitized
1005
Split sentences and pre-order words in the digitized text into segments having reduced complexity relative to unsplit sentences
1010
Recognize words in the digitized text that match entries in a named entity table
1015
Match segments to entries in a translation memory database of existing clinical trial documents that are translated from the source natural language to at least partially translate the matched segment from the source natural language to the target natural language
1020
Apply transformational grammar to the digitized text to produce a single representation of sentences in the clinical trial documents that share a common meaning
1025
Provide, as an output, a machine-understandable representation of the source natural language text that includes semantic meaning
1030

1300
CPU
1302
Network
I/F
1316
I/O
controller
1318
1310
Memory
1304
RAM
1306
ROM
1308
Mass storage
device
1312

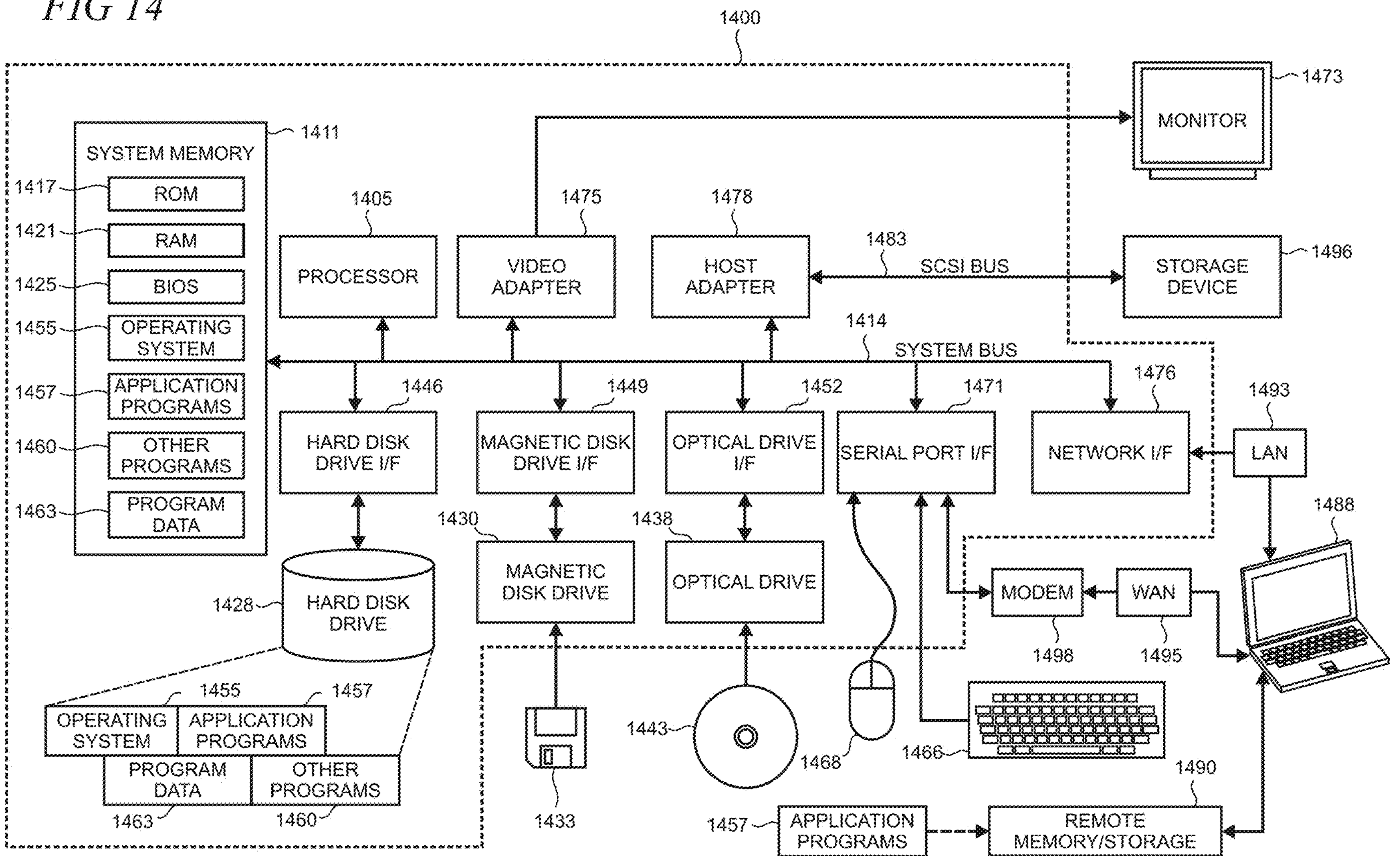
FIG 14
1400
SYSTEM MEMORY
1411
1417
ROM
1421
RAM
1425
BIOS
1455
OPERATING SYSTEM
1457
APPLICATION PROGRAMS
1460
OTHER PROGRAMS
1463
PROGRAM DATA
1405
PROCESSOR
1475
VIDEO ADAPTER
1478
HOST ADAPTER
1483
SCSI BUS
MONITOR
1473
STORAGE DEVICE
1496
1414
SYSTEM BUS
1446
HARD DISK DRIVE I/F
1449
MAGNETIC DISK DRIVE I/F
1452
OPTICAL DRIVE I/F
1471
SERIAL PORT I/F
1476
NETWORK I/F
1493
LAN
1488
1428
HARD DISK DRIVE
1430
MAGNETIC DISK DRIVE
1438
OPTICAL DRIVE
MODEM
1498
WAN
1495
1455
1457
OPERATING SYSTEM
APPLICATION PROGRAMS
PROGRAM DATA
OTHER PROGRAMS
1463
1460
1433
1443
1468
1466
1490
1457
APPLICATION PROGRAMS
REMOTE MEMORY/STORAGE

AUTOMATED TRANSLATION OF SUBJECT MATTER SPECIFIC DOCUMENTS

CROSS-REFERENCE TO RELATED APPLICATION

This application is a continuation of U.S. Ser. No. 16/276,002 filed on Feb. 14, 2019, now U.S. Pat. No. 10,839,164 which claims the benefit of U.S. Provisional Application Ser. No. 62/739,541 filed on Oct. 1, 2018, the entire content of which is hereby incorporated by reference in its entirety.

BACKGROUND

Language translation involves the conversion of sentences from one natural language (i.e., a language that has developed naturally through use, as contrasted with artificial language or computer code), usually referred to as the "source" language, into another language, typically called the "target" language. When performed by a machine (e.g., a computer) such translation is referred to as automated language translation or machine translation.

SUMMARY

Documents in a source natural language are translated into one or more target natural languages using a computer-implemented translation tool that is configured to operate within the domain of the subject matter that impose specialized requirements for translation and readability. Subject matter specific documents typically include domain-specific terminology, are subject to various regulatory guidelines, and have different readability requirements depending on the intended reader (for example, doctor vs. patient, adult vs. child). The computer-implemented translation tool applies machine-learning techniques that deconstruct elements of a document into a standardized data structure and perform pre-processing steps to parse digitized document text to identify the correct sentence structures for the target natural language to optimize translation by a translation engine such as a neural machine translation engine. The tokens that are input into the neural machine translation engine are generated to be semantically meaningful in the target natural language to thereby enhance the understanding of the neural machine translation engine.

Tokens are transmitted over an application programming interface (API) to the neural machine translation engine in a specific order. Machine learning techniques are applied to post process the translated tokens returned from the neural machine translation engine to correct ontology in the semantic domains of Subject matter specific terminology. The translation tool reconstructs the document in the target natural language using the ordered translated tokens with corrected ontology to maintain characteristics of the original document including, for example, format, layout, images (e.g., pictures, photographs, illustrations, etc.), and other content (e.g., diagrams, tables, graphs, charts, etc.). The pre-processing techniques (prior to the machine translation) and post-processing techniques (after machine translation) vary based on the characteristics of the language and its complexity for machine translation (e.g., word order can be relatively free because of the morphology of the German language, Russian is a highly inflected language, Japanese has different writing systems). The machine translated text is subject to adjustments from a human operator through a user interface that is exposed on the translation tool. The adjustments can be used to improve the translation of a specific document and may be used as a machine learning input to improve performance of the translation tool in general.

In various illustrative examples, the pre-processing of the document comprises sentence splitting and simplification, named entity recognition, fast fuzzy matching with existing translated documents in a translation memory database, and application of transformational grammar. A cascade of finite-state transducers is configured to perform sentence splitting that feeds a speech tagger (described below). The sentence splitting and simplification processing generates ordered tokens that are semantically meaningful. The structure of the processed sentences is typically less complex than the original text.

The named entity recognition processing identifies text that may be excluded from translation or which requires translation utilizing a user-defined glossary. Named entities can include proper nouns (e.g., company names, family names, city names), abbreviations, and acronyms that are matched against data stored in a table or database. The process can include classification of named entities into pre-defined classes, and extraction of confidential information can be masked.

The named entity recognition processing can further enhance opportunities for matching tokens to existing translated documents in translation memory. Use of the translation memory enables some portions of the original text to be translated based on historical documents prior to transmission to the neural machine translation engine over the API. The matching can be implemented using fuzzy logic in which matches between document text and the translation memory can be less than 100 percent.

A speech tagger is utilized to implement the transformational grammar processing which identifies parts of speech in the document text while providing a single representation of sentences that have a common meaning using a series of transformations. The transformations can include detecting a passive voice sentence and transforming the detected passive voice sentence into an active voice sentence. An indirect sentence form may be detected and transformed into a direct sentence form. A transformation in which words in a sentence are re-ordered based on sentence structure requirements of the target natural language may also be implemented.

The present computer-implemented translation tool provides improvements in the underlying operation of the computing device on which it executes by providing for increased translation accuracy. More specifically, the utilization of the pre-processing enables efficient utilization of processing cycles, memory requirements, and network bandwidth by creating input to the neural machine translation engine that results in accurate output and reduces the need to redo translations or discard poor results. The translation tool further enhances the efficiency of the human-machine interface on the computing device because the tool produces a more complete and accurate translation compared with conventional methodologies. The translation tool produces translated documents quickly with a high degree of correctness including grammar that is target language-appropriate with the proper utilization of specialized and domain-specific phrases and terms. A human translator's interaction with the translation tool can thus be focused on adjusting and refining the new translated document produced by the tool to leverage the translator's time and language expertise to optimal advantage.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings. The term clinical trial will be used throughout the Detailed Description as an example or substitute for any subject matter specific document.

DESCRIPTION OF THE DRAWINGS

FIG. 3 shows illustrative details of natural language structuring pre-processing that is utilized in the computer-implemented translation tool;

FIGS. 10, 11, and 12 show illustrative methods for automated translation of clinical trial documents;

FIG. 14 is a simplified block diagram of an illustrative computing device that may be used at least in part to implement the present automated translation of clinical trial documents.

Like reference numerals indicate like elements in the drawings. Elements are not drawn to scale unless otherwise indicated.

DETAILED DESCRIPTION

Figure 1:
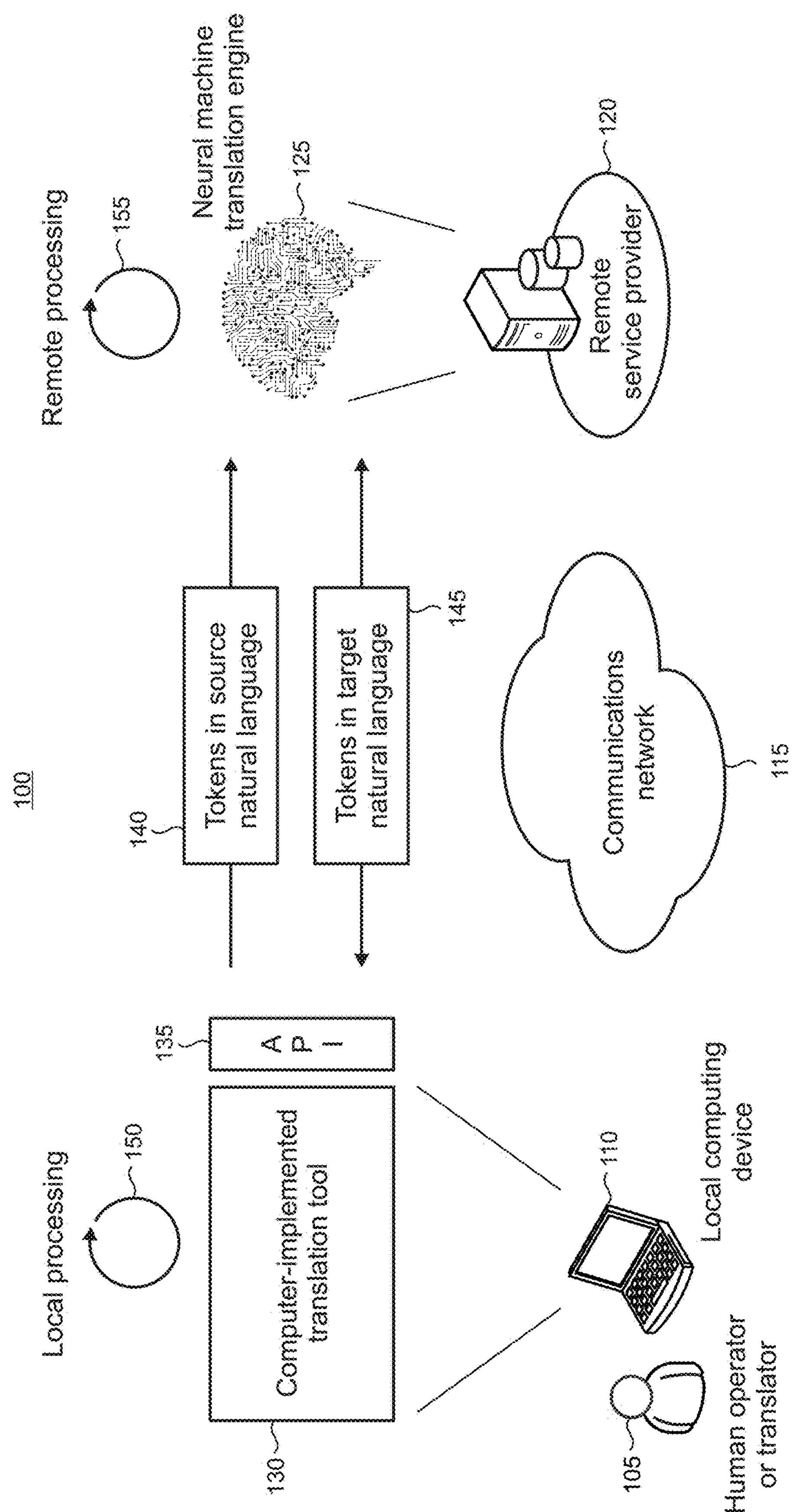
FIG. 1 shows an illustrative computing environment in which a computer-implemented translation tool executes on a computing device.

FIG. 1 shows an illustrative computing environment 100 in which a human operator or translator 105 employs a computing device 110 that is configured to communicate over a communications network 115 with a remote service provider 120 that supports a neural machine translation engine 125. In alternative implementations, the translation engine may be implemented using a statistical model or a combination of statistical and neural modeling. In addition, the neural machine translation engine may be supported locally, for example, by an entity or enterprise that supports the computing device and operator or using a combination of local and remote support.

The computing device 110 hosts a computer-implemented translation tool 130 that may be implemented, for example, as a software application that executes on the device. In alternative implementations, the translation tool may be implemented using hardware, firmware, or a combination thereof, depending on the needs of a particular implementation of the present automated translation of clinical trial documents.

In this illustrative example, the computer-implemented translation tool communicates over the network 115 through an application programming interface (API) with the neural machine translation engine 125. As described in more detail below, the translation tool sends tokens 140 over an application programming interface (API) 135 that are expressed in a source natural language to the neural machine translation engine and receives tokens 145 that are expressed in a target natural language that is different from the source. Thus, the neural machine translation engine translates a token from one language (i.e., the source language) to another (i.e., the target language). While this illustrative example uses a combination of processing at the local computing device (as indicated by reference numeral 150) and processing by the remote service provider 120 (as indicated by reference numeral 155) to provide a complete solution for automated translation of clinical trial documents, it is noted that other processing allocations and arrangements may also be utilized. For example, the translation tool may be instantiated as a remote or cloud-based application. Various combinations of local and remote processing can be implemented as appropriate for a given translation tool implementation.

The computing device 110 comprises an electronic device such as a personal computer, server, handheld device, workstation, multimedia console, smartphone, tablet computer, laptop computer, or the like. In the discussion that follows, the use of the term "computing device" is intended to cover all electronic devices that perform some computing operations, whether they be implemented locally, remotely, or by a combination of local and remote operation.

The communications network 115 can include any of a variety of network types and network infrastructure in various combinations or sub-combinations including local-area networks (LANs), wide-area networks (WANs), cellular networks, satellite networks, IP (Internet-Protocol) networks such as Wi-Fi under IEEE 802.11 and Ethernet networks under IEEE 802.3, a public switched telephone network (PSTN), and/or short-range networks such as Bluetooth® networks. Network infrastructure can be supported, for example, by mobile operators, enterprises, Internet service providers (ISPs), telephone service providers, data service providers, and the like. The communications network 115 may utilize portions of the Internet (not shown) or include interfaces that support a connection to the Internet so that the computing device 110 can access data or content and/or render user experiences supported by the remote service provider and/or other service providers (not shown).

Figure 2:
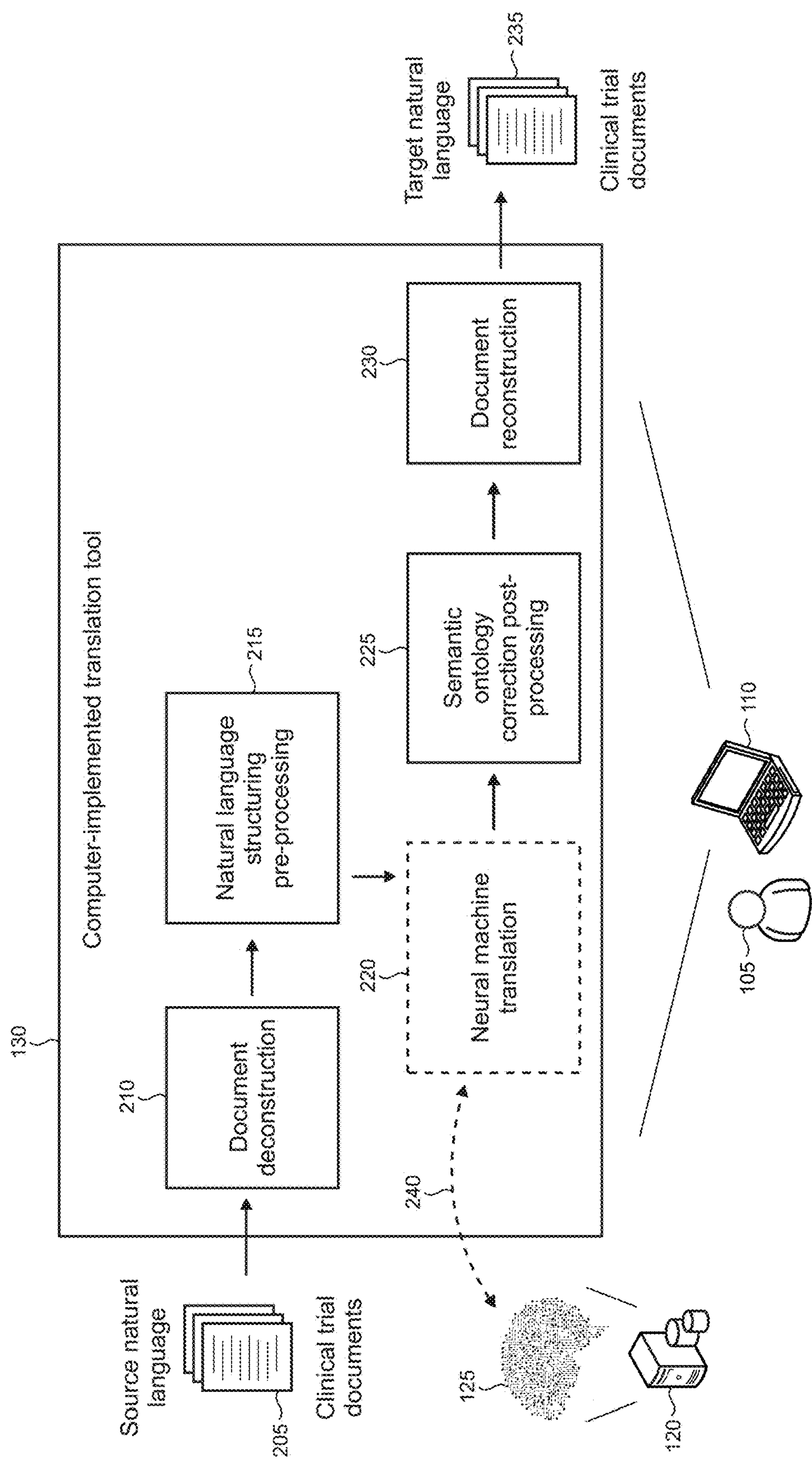
FIG. 2 shows illustrative details of the computer-implemented translation tool.

FIG. 2 shows illustrative details of the computer-implemented translation tool 130 that may be utilized to process one or more clinical trial documents 205 as inputs that are expressed in a given source natural language. The translation tool implements multiple stages of processing including document deconstruction 210, natural language structuring pre-processing 215, neural machine translation 220, semantic ontology correction post-processing 225, and document reconstruction 230. As shown, the output of the translation tool is a corresponding one or more translated clinical trial documents 235 that are expressed in a given target natural language. Neural machine translations are currently available for many language pairs and the number is expected to increase. While English is commonly one of the languages in a pair, non-English language pairs are also expected to become more widely supported.

Document deconstruction 210 includes converting the source clinical trial documents 205 to a digitized form that uses a standardized data structure across all documents. The quality of the source materials may be expected to vary widely in typical implementations. Thus, the document deconstruction stage can apply various techniques to accommodate noise and unwanted artifacts during digitization to improve quality of the input to the translation tool 130. In some cases, relevant descriptive information such as metadata can be collected for the input clinical trial documents and stored. Such information may be used, for example, for clinical trial document management and other purposes.

The natural language structuring pre-processing stage 215 provides tokenization of the digitized clinical trial documents 205 to provide for optimized neural machine translation. The pre-processing stage is described in more detail in the description below that accompanies FIGS. 3-8. The neural machine translation stage 220, as noted above, may be supported by interactions with the neural machine translation engine 125 supported by the remote service provider 120, as indicated by the dashed line 240. The neural machine translation stage 220 translates the tokens provided by the pre-processing stage and returns the translated tokens to the semantic ontology correction post-processing stage 225. In post-processing, the individual translated tokens from the neural machine translation are corrected to account for phrases, terms, acronyms, and other domain-specific language that is used in the clinical trial or medical domains. The document reconstruction stage 230 operates to maintain the formatting of the original source document in the translated output documents 235 in the target language. The document reconstruction stage can also be configured to persist other characteristics across the documents (i.e., from source input to target output) including images (e.g., pictures, photographs, illustrations, etc.), and other content (e.g., diagrams, tables, graphs, charts, etc.).

FIG. 3 shows illustrative details of the natural language structuring pre-processing stage 215 that is utilized in the computer-implemented translation tool. The inputs to the pre-processing stage include a digitized clinical trial document 305 that is expressed in a source natural language. The pre-processing stage includes four constituent elements including sentence splitting and simplification 310, named entity recognition 315, fast fuzzy matching 320, and transformational grammar 325. In typical implementations the processing is performed sequentially with sentence splitting performed first, then named entity recognition and fast fuzzy matching, and followed by transformational grammar. However, in alternative implementations, the processing may be performed in parallel, in a combination of series and parallel, in another sequence, or in various combinations thereof. Generally, sentence splitting and simplification is the first processing that is performed which feeds the other constituent elements in the pre-processing stage. The output of the natural language structuring pre-processing stage 215 includes tokens 330 in the source natural language that are arranged as an ordered output 335.

Figure 4:
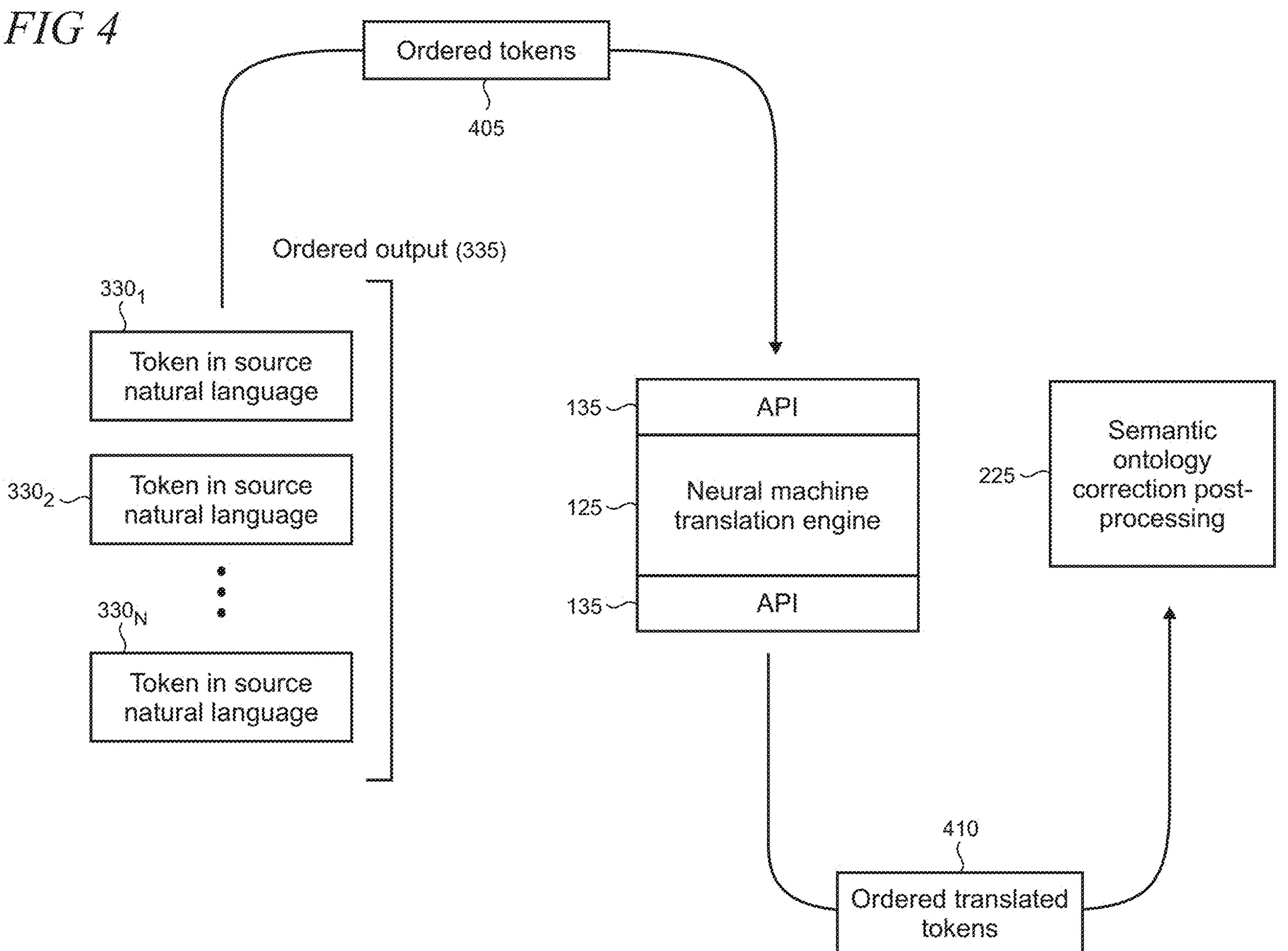
FIG. 4 shows an illustrative arrangement in which tokens are provided as an ordered input to a neural machine translation engine.

FIG. 4 shows that the ordered output 335 from the natural language structuring pre-processing stage is utilized so that ordered tokens 405 are provided as an input to the neural machine translation engine 125 via the API 135. That is, the output from the natural language structuring pre-processing stage is provided token-by-token to preserve the order. The neural machine translation engine translates the tokens from source to target language and preserves the order when supplying the ordered translated tokens 410 to the semantic ontology correction post-processing stage 225.

Figure 5:
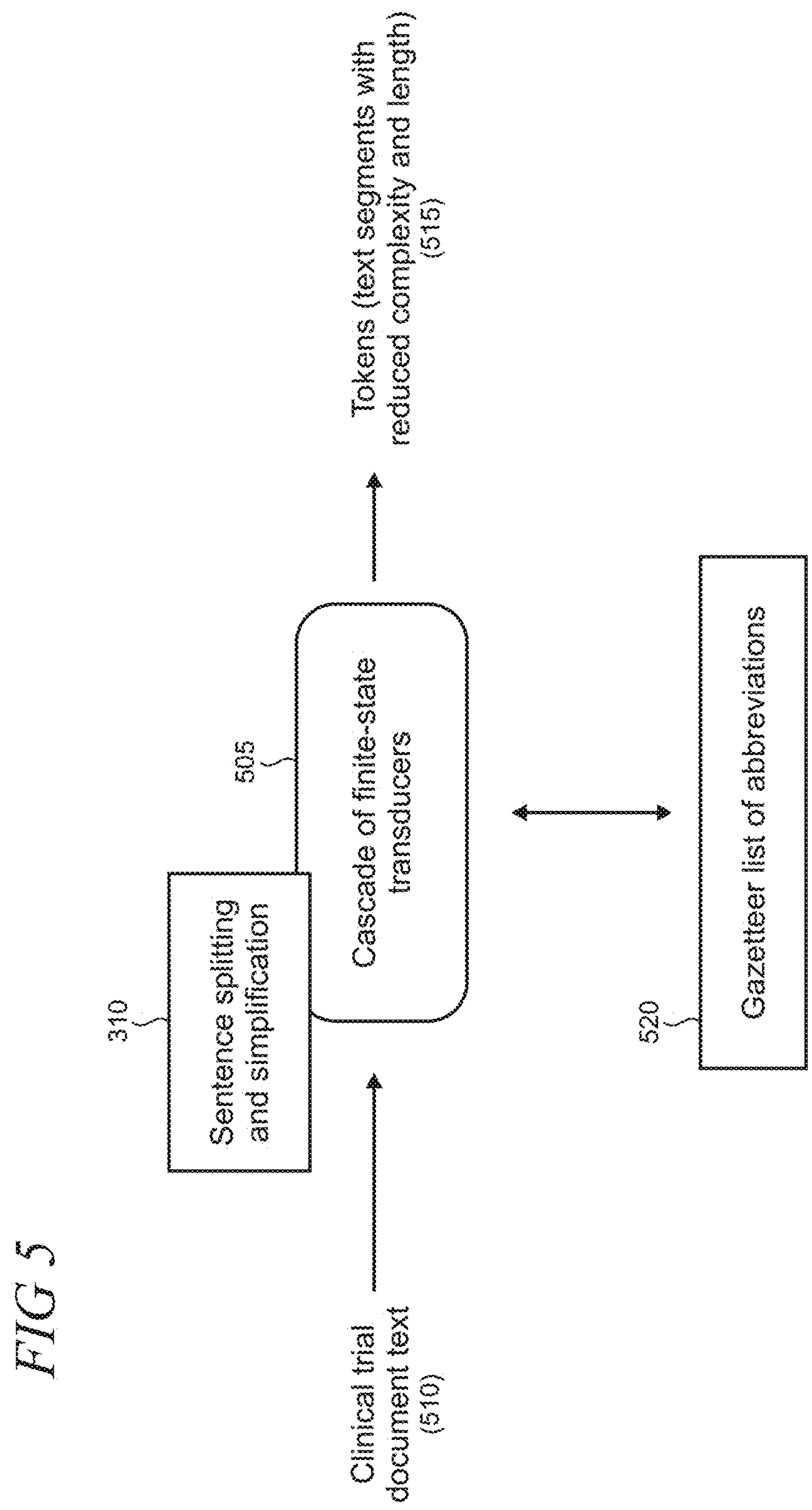
FIG. 5 shows an illustrative finite-state transducer cascade that is used to implement sentence splitting and simplification.

FIG. 5 shows an illustrative finite-state transducer (FST) cascade 505 that may be used to implement sentence splitting and simplification element 310 of the natural language structuring pre-processing stage 215 (FIG. 2). FST cascades are well adapted to represent the tokenization paths in the linguistic patterns that may be commonly encountered in clinical trial documents. Sentence splitting is performed before subsequent text processing is performed to break up the input text into distinct and meaningful units. Splitting would be straightforward to accomplish if the source natural language is perfectly punctuated. However, even when expressed in well punctuated languages, the source clinical trial document text 510 will typically include ambiguities that will result in multiple tokenization options for dividing one meaningful unit from an adjacent meaningful unit. To improve tokenization performance, the FST cascade 505 uses a gazetteer list of abbreviations 520 to help distinguish sentence-marking full stops from other markings.

The FST cascade 505 provides tokens 515 that comprise text segments that have reduced complexity and length compared with the source text. The tokens identify key sentence structures that can improve translation performance by the neural machine translation engine 125 (FIG. 1) by being semantically meaningful. In addition, as noted above, the FST cascade provides the tokens as an ordered output for translation by the neural machine translation engine.

Figure 6:
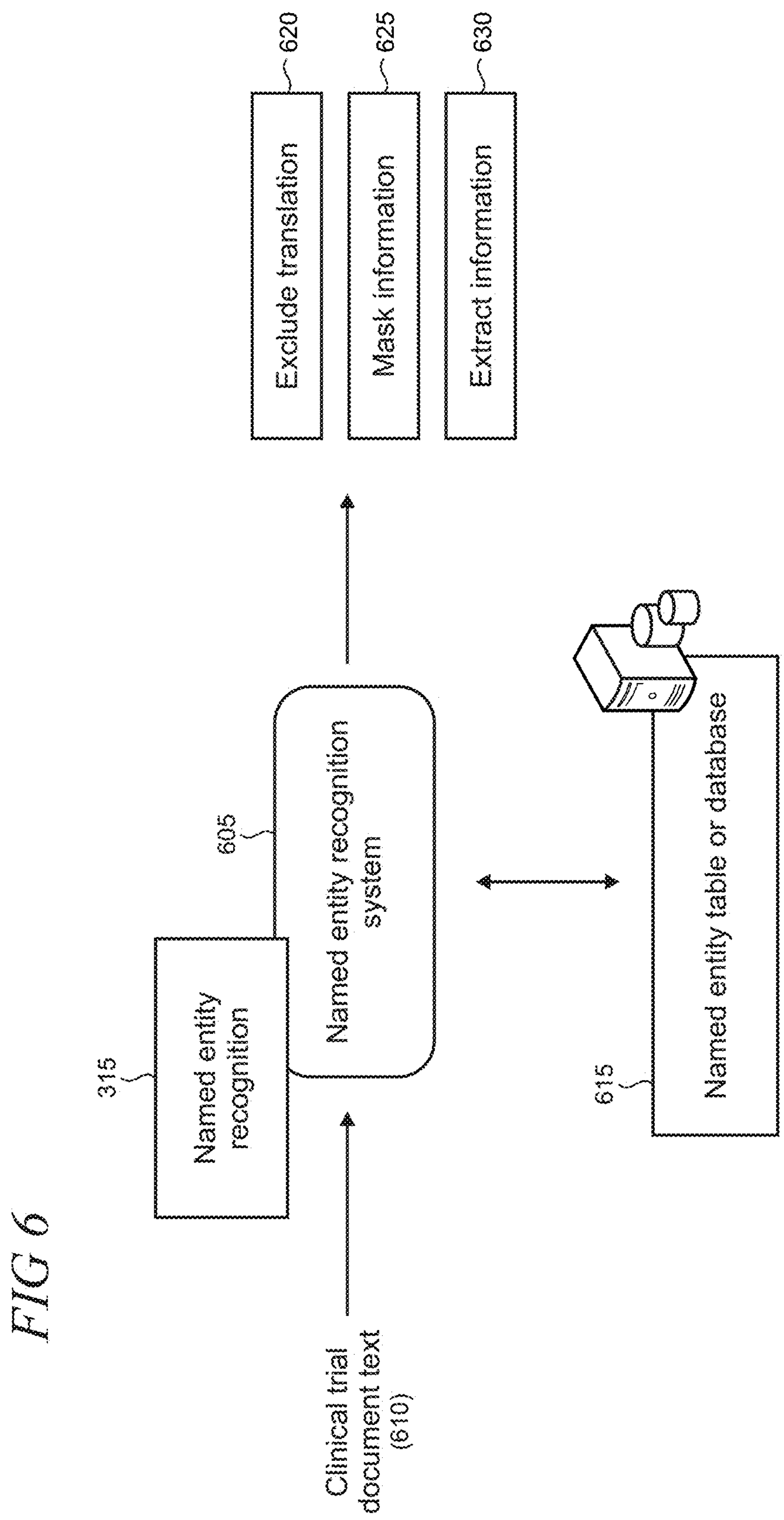
FIG. 6 shows an illustrative named entity recognition system.

FIG. 6 shows an illustrative named entity recognition system 605 that may be used to implement the named entity recognition element 315 of the natural language structuring pre-processing stage 215 (FIG. 2). Named entities may create problems for machine translation systems and can cause translation failures that impact overall morphosyntactic well-formedness of sentences and word sense disambiguation in the source clinical trial document text. The named entity recognition system 605 employs methodologies that implement different approaches to translation of named entities compared with other types of words. For example, foreign person names in Russian should be transcribed and written in Cyrillic, and names that coincide with common nouns should not be looked up in the general dictionary.

The named entity recognition system 605 is configured to compare clinical trial document text 610 against entries in a named entity table or database 615. The system can use the results in various ways such as excluding named entities from translation 620, for example, names of organizations. Such selective translation exclusion may help to maximize opportunities to match document text with translation memory, as described below. Recognized information, such as confidential information or personally identifiable information, can be masked 625. Recognized information can also be extracted 630 from the source document and used for various purposes. In some cases, information that is excluded from translation by the neural machine translation engine 125 (FIG. 1) can be translated using a user-defined glossary.

Figure 7:
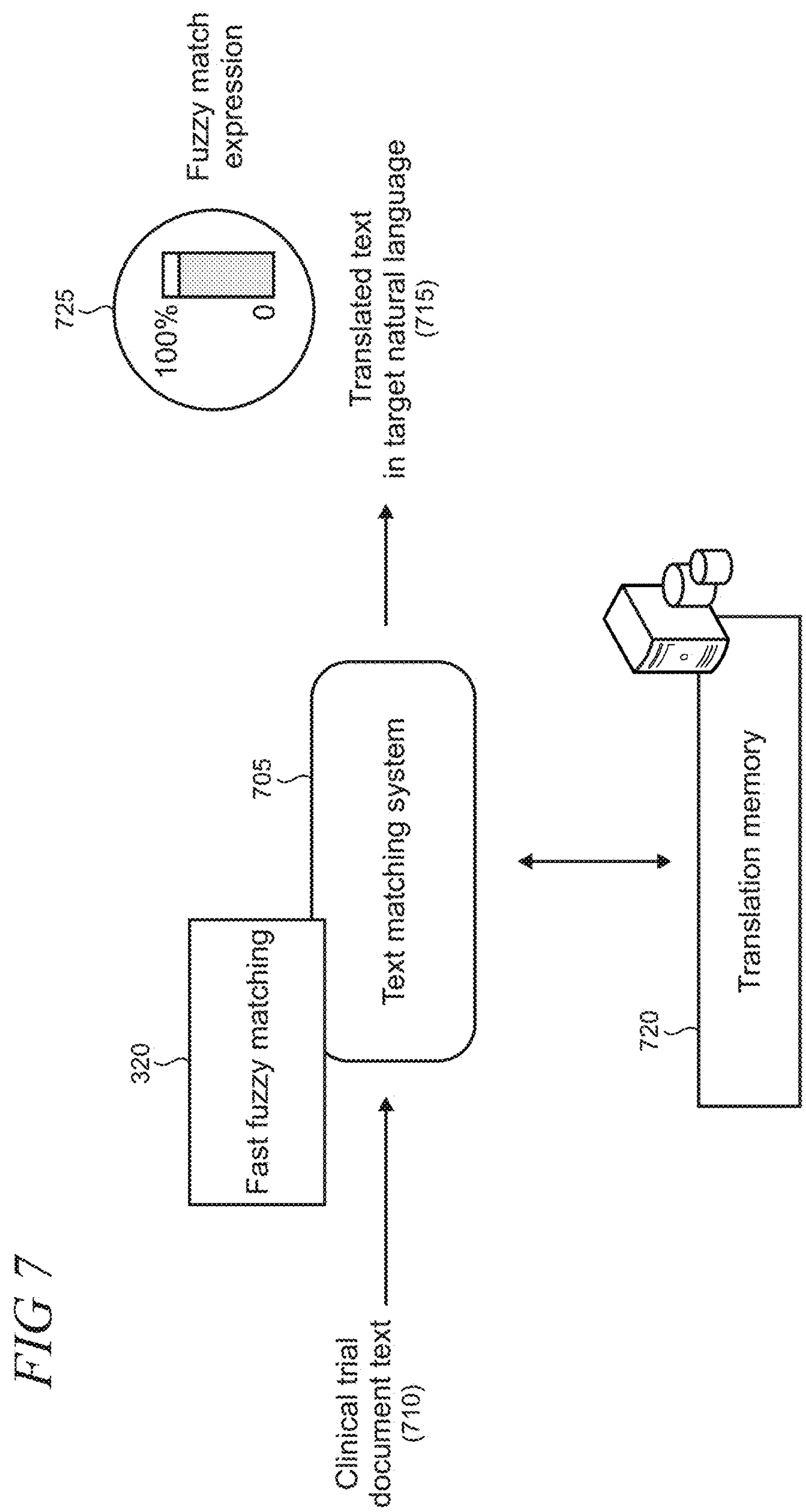
FIG. 7 shows an illustrative text matching system that is used to implement fast fuzzy matching with a translation memory.

FIG. 7 shows an illustrative text matching system 705 that may be used to implement the fast fuzzy matching 320 element of the natural language structuring pre-processing stage 215 (FIG. 2) in which clinical trial document text 710 is compared against entries in a translation memory 720. The translation memory includes existing translated clinical trial documents that can be matched against source text to thereby generate translated text 715 using a separate process from the neural machine translation engine 125 (FIG. 1). The matching can be implemented using fuzzy logic in which matches between document text and the translation memory can be less than 100 percent. The text matching system can provide an expression 725 of the fuzzy match in some implementations. Translation memory matches are expressed as percentages in which a perfect match is a 100% match, and fuzzy matches are less than 100% matches.

The translation memory 720 can be optimized by processing existing translated clinical trial documents to remove incorrect or confusing language conversions that do not make sense. Such optimization can improve matching effectiveness and increase document translation accuracy. The text matching system 705 can be implemented using fast search algorithms that enable performant matching by improving the retrieval of salient information from the translation memory which can be large.

Figure 8:
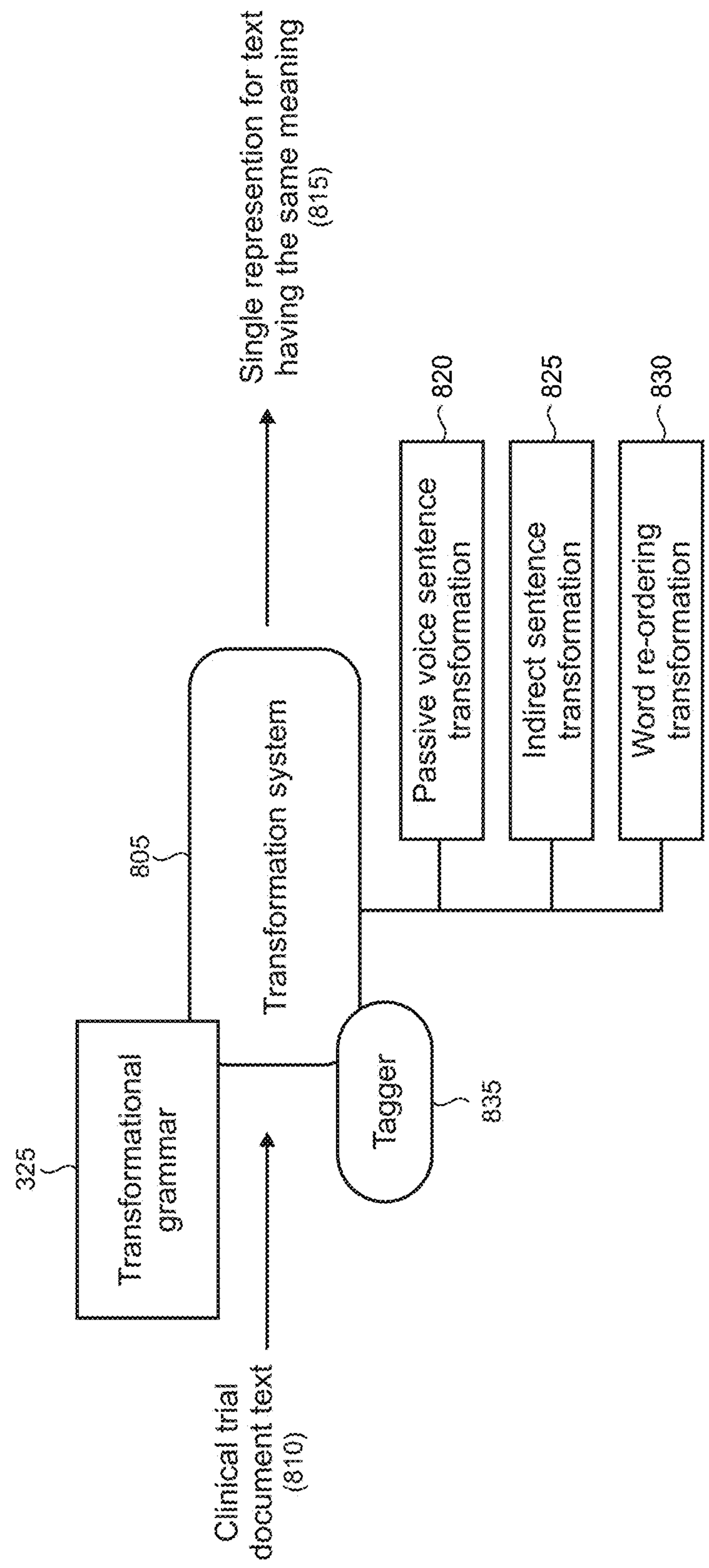
FIG. 8 shows an illustrative transformation system.

FIG. 8 shows an illustrative transformation system 805 that may be used to implement the transformational grammar element 325 in the natural language structuring pre-processing stage 215 (FIG. 2). The transformation system is configured to transform clinical trial document text 810 into a single representation for text that has the same meaning 815 using a series of transformations. The transformation system 805 also exposes a tagger 835 that is configured to identify and tag information for parts of speech of the clinical trial document text such as verb, noun, adjective, etc.

As shown, the transformations include a passive voice sentence transformation 820 in which passive voice sentences are detected and transformed into active voice sentences. An indirect sentence transformation 825 detects indirect sentences and transforms them into direct sentences. A word re-ordering transformation 830 re-orders words in the source document text according to language structures that are appropriate for the target language, for example, to accommodate the more formalized layout of the sentence in German as compared to Spanish.

Figure 9:
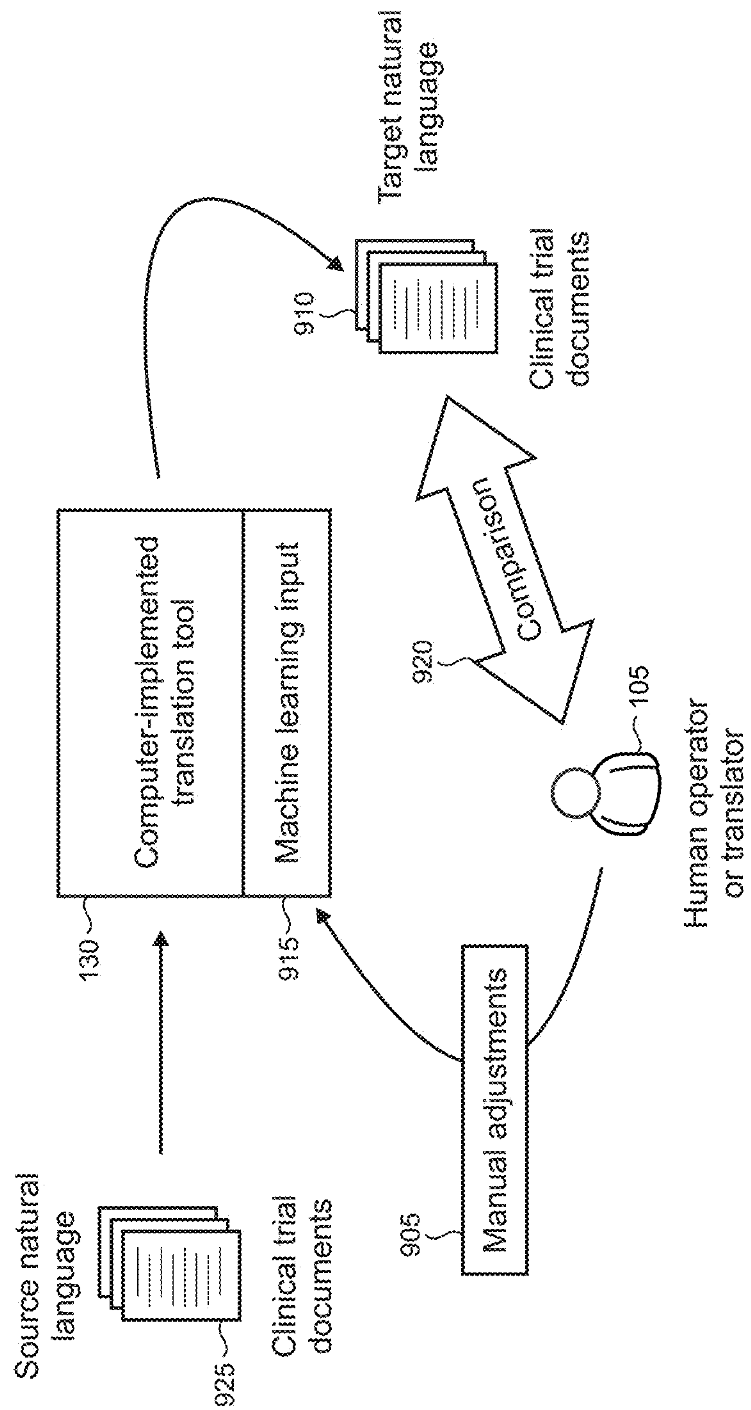
FIG. 9 shows illustrative manual adjustments to a translated clinical trial document that may be utilized as machine learning input.

FIG. 9 shows illustrative manual adjustments 905 to a translated clinical trial document 910 that may be utilized as machine learning input 915 to the computer-implemented translation tool 130. In this example, the human translator can perform a comparison 920 between the translated clinical trial document in the target natural language and the original clinical trial document 925 in the source natural language. The translator may make adjustments to the document that the translation tool can analyze to make appropriate changes in the underlying automated translation processes. Alternatively, the translator may directly adjust the processes themselves to achieve a desired outcome. In some cases, the translator may perform multiple translation iterations to assist the machine-learning process by specifying different translation outcomes, or varying processing parameters with each iteration.

Figure 11:
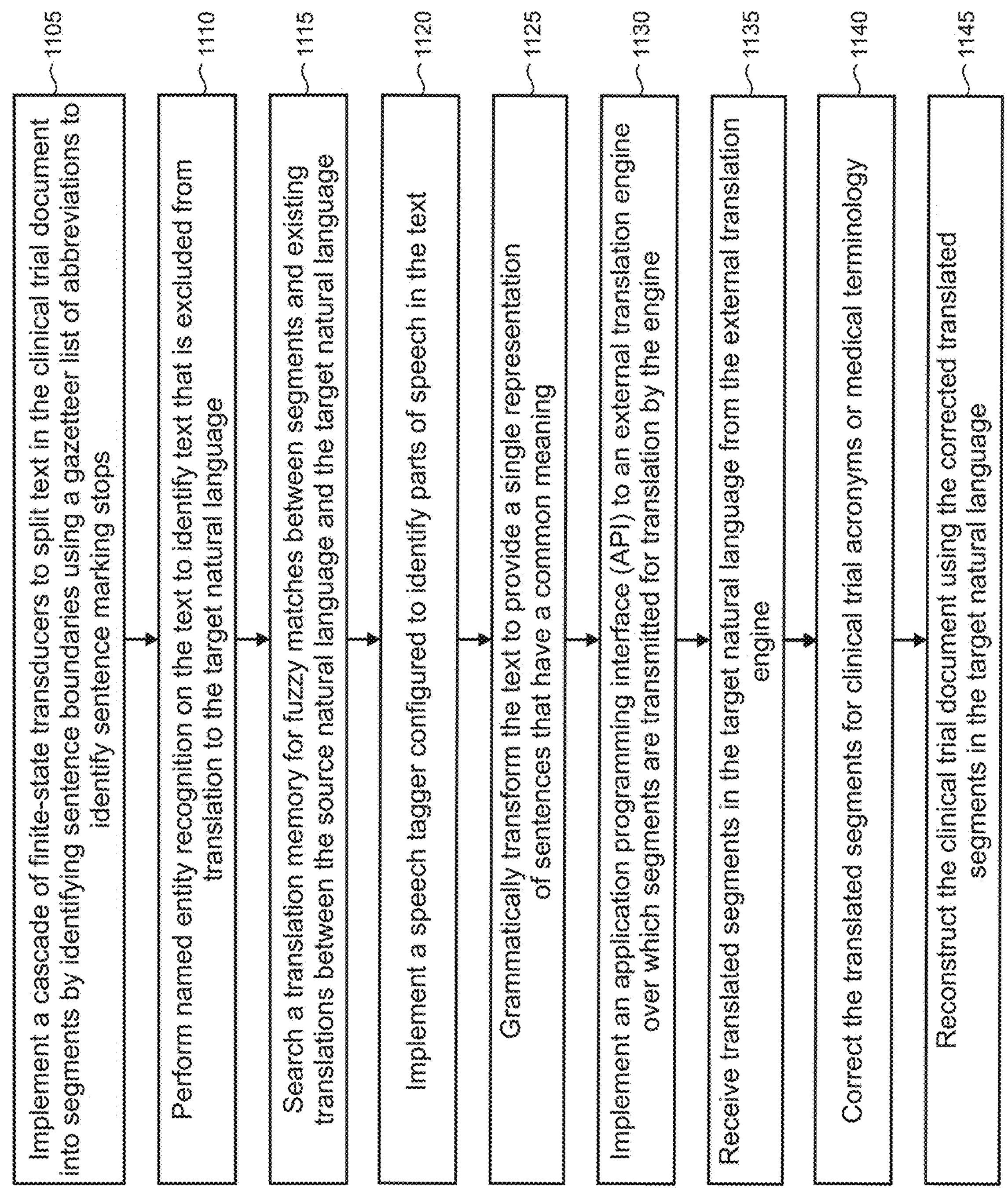
Figure 12:
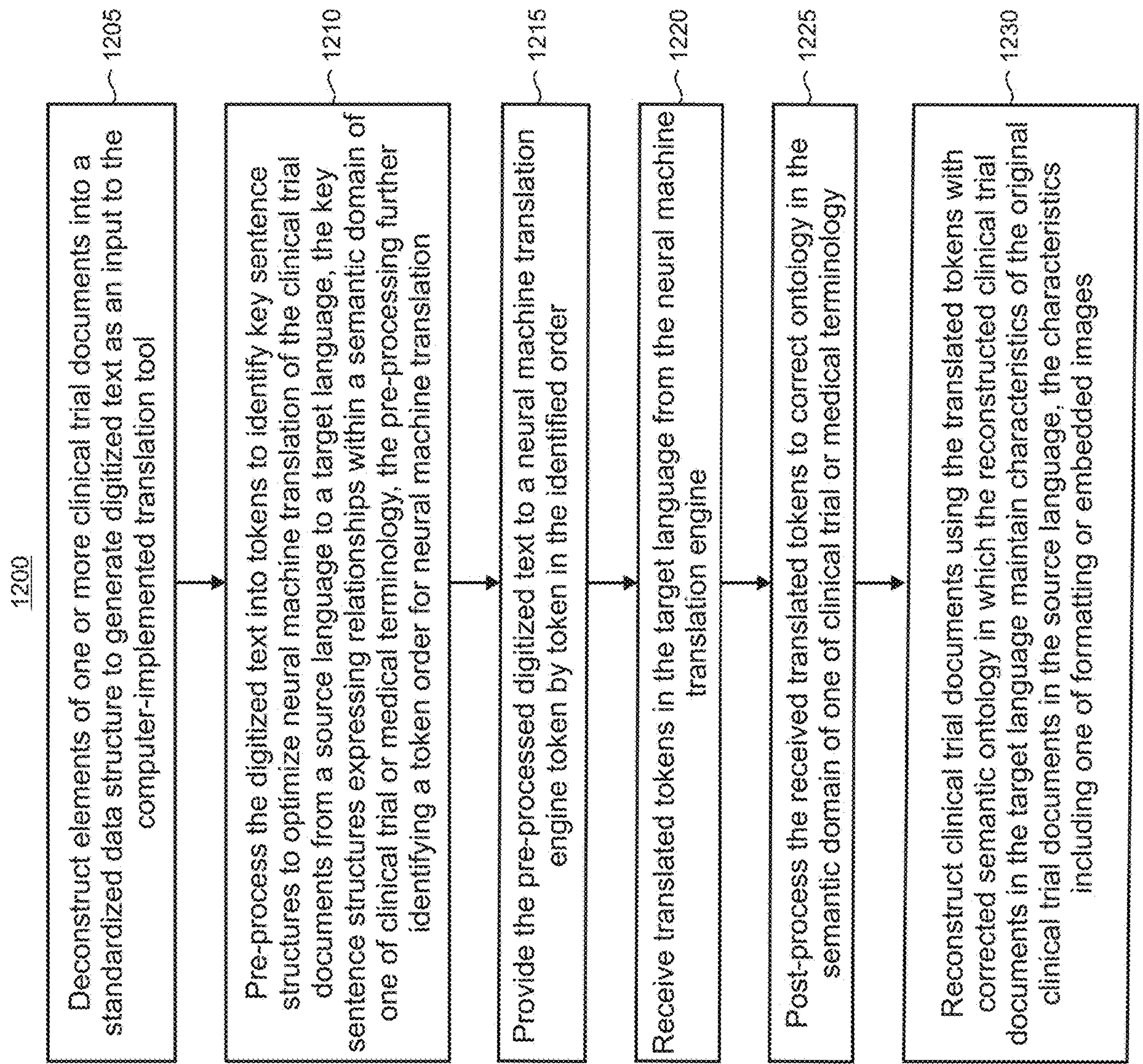

FIGS. 10, 11, and 12 show illustrative methods for automated translation of clinical trial documents. Unless specifically stated, methods or steps shown in the flowcharts and described in the accompanying text are not constrained to a particular order or sequence. In addition, some of the methods or steps thereof can occur or be performed concurrently and not all the methods or steps have to be performed in a given implementation depending on the requirements of such implementation and some methods or steps may be optionally utilized.

FIG. 10 is a flowchart of an illustrative method 1000 that may be performed by a computing device that executes an automated translation tool for translating a clinical trial document from a source natural language to a target natural language. In step 1005, the device receives, as an input, an electronic representation of the clinical trial document in a source natural language in which text of the clinical trial document is digitized. In step 1010, the device splits sentences and pre-orders words in the digitized text into segments having reduced complexity relative to unsplit sentences. In step 1015, the device recognizes words in the digitized text that match entries in a named entity table. In step 1020, the device matches segments to entries in a translation memory database of existing clinical trial documents that are translated from the source natural language to at least partially translate the matched segment from the source natural language to the target natural language. In step 1025, the device applies transformational grammar to the digitized text to produce a single representation of sentences in the clinical trial documents that share a common meaning. In step 1030, the device provides, as an output, a machine-understandable representation of the source natural language text that includes semantic meaning.

FIG. 11 is a flowchart of an illustrative method 1100 that may be performed by a computing device that executes an automated translation tool for translating a clinical trial document expressed in a source natural language to a target natural language. In step 1105, the device implements a cascade of finite-state transducers to split text in the clinical trial document into segments by identifying sentence boundaries using a gazetteer list of abbreviations to identify sentence marking stops. In step 1110, the device performs named entity recognition on the text to identify text that is excluded from translation to the target natural language. In step 1115, the device searches a translation memory for fuzzy matches between segments and existing translations between the source natural language and the target natural language. In step 1120, the device implements a speech tagger configured to identify parts of speech in the text. In step 1125, the device grammatically transforms the text to provide a single representation of sentences that have a common meaning. In step 1130, the device implements an application programming interface (API) to an external translation engine over which segments are transmitted for translation by the engine. In step 1135, the device receives translated segments in the target natural language from the external translation engine. In step 1140, the device corrects the translated segments for clinical trial acronyms or medical terminology. In step 1145, the device reconstructs the clinical trial document using the corrected translated segments in the target natural language.

FIG. 12 is a flowchart of an illustrative method 1200 that may be performed by a computing device that executes an automated translation tool. In step 1205, the device deconstructs elements of one or more clinical trial documents into a standardized data structure to generate digitized text as an input to the computer-implemented translation tool. In step 1210, the device pre-processes the digitized text into tokens to identify key sentence structures to optimize neural machine translation of the clinical trial documents from a source language to a target language, the key sentence structures expressing relationships within a semantic domain of one of clinical trial or medical terminology, the pre-processing further identifying a token order for neural machine translation. In step 1215, the device provides the pre-processed digitized text to a neural machine translation engine token by token in the identified order. In step 1220, the device receives translated tokens in the target language from the neural machine translation engine. In step 1225, the device post-processes the received translated tokens to correct ontology in the semantic domain of one of clinical trial or medical terminology. In step 1230, the device reconstructs clinical trial documents using the translated tokens with corrected semantic ontology in which the reconstructed clinical trial documents in the target language maintain characteristics of the original clinical trial documents in the source language, the characteristics including one of formatting or embedded images.

Figure 13:
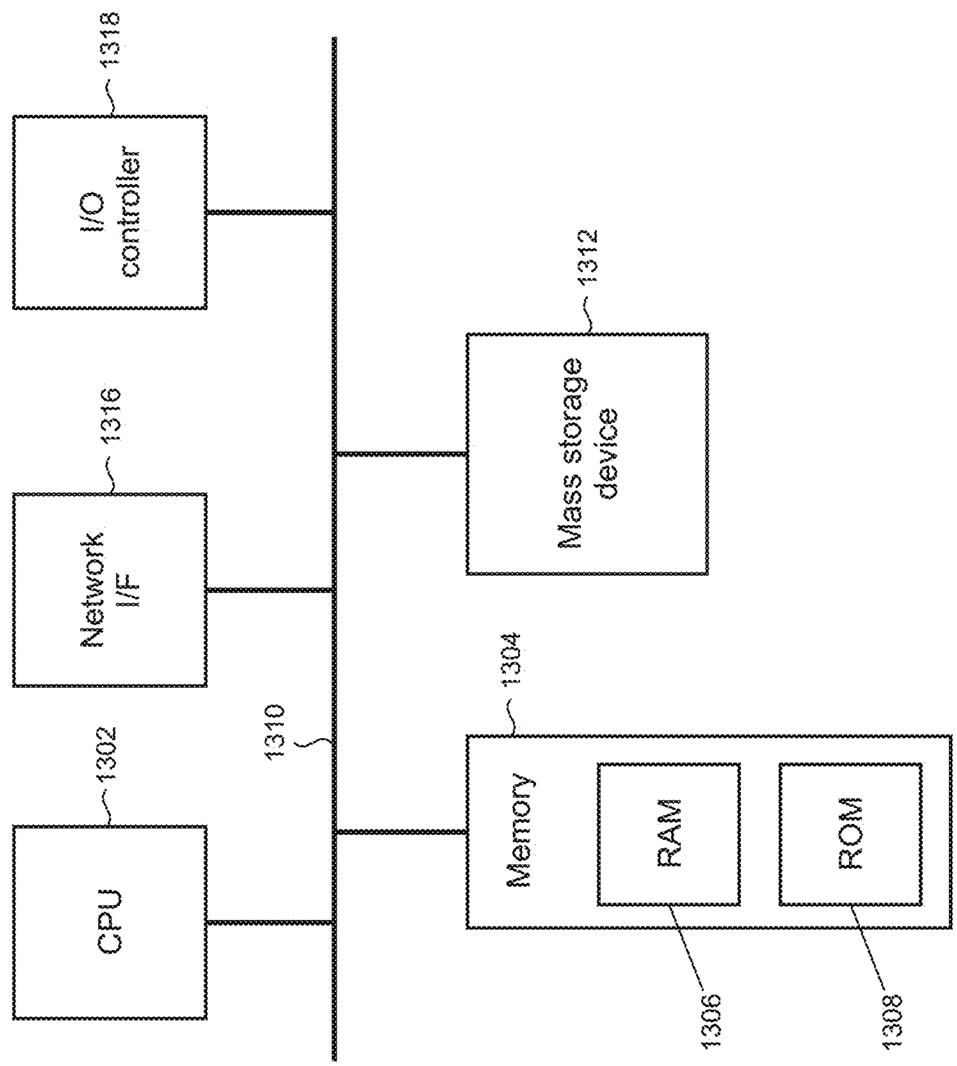
FIG. 13 is a block diagram of an illustrative computing device that may be used at least in part to implement the present automated translation of clinical trial documents.

FIG. 13 shows an illustrative architecture 1300 for a device, such as a server, capable of executing the various components described herein for the present automated translation of clinical trial documents. The architecture 1300 illustrated in FIG. 13 includes one or more processors 1302 (e.g., central processing unit, dedicated artificial intelligence chip, graphic processing unit, etc.), a system memory 1304, including RAM (random access memory) 1306 and ROM (read only memory) 1308, and a system bus 1310 that operatively and functionally couples the components in the architecture 1300. A basic input/output system containing the basic routines that help to transfer information between elements within the architecture 1300, such as during startup, is typically stored in the ROM 1308. The architecture 1300 further includes a mass storage device 1312 for storing software code or other computer-executed code that is utilized to implement applications, the file system, and the operating system. The mass storage device 1312 is connected to the processor 1302 through a mass storage controller (not shown) connected to the bus 1310. The mass storage device 1312 and its associated computer-readable storage media provide non-volatile storage for the architecture 1300. Although the description of computer-readable storage media contained herein refers to a mass storage device, such as a hard disk, solid state drive, or optical drive, it may be appreciated that computer-readable storage media can be any available storage media that can be accessed by the architecture 1300.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read only memory), EEPROM (electrically erasable programmable read only memory), Flash memory or other solid state memory technology, CD-ROM, DVDs, HD-DVD (High Definition DVD), Bluray, or other optical storage, magnetic cassettes, magnetic tape, magnetic disk storage or other magnetic storage devices, or any other medium which can be used to store the desired information and which can be accessed by the architecture 1300.

According to various embodiments, the architecture 1300 may operate in a networked environment using logical connections to remote computers through a network. The architecture 1300 may connect to the network through a network interface unit 1316 connected to the bus 1310. It may be appreciated that the network interface unit 1316 also may be utilized to connect to other types of networks and remote computer systems. The architecture 1300 also may include an input/output controller 1318 for receiving and processing input from several other devices, including a keyboard, mouse, touchpad, touchscreen, control devices such as buttons and switches or electronic stylus (not shown in FIG. 13). Similarly, the input/output controller 1318 may provide output to a display screen, user interface, a printer, or other type of output device (also not shown in FIG. 13).

It may be appreciated that the software components described herein may, when loaded into the processor 1302 and executed, transform the processor 1302 and the overall architecture 1300 from a general-purpose computing system into a special-purpose computing system customized to facilitate the functionality presented herein. The processor 1302 may be constructed from any number of transistors or other discrete circuit elements, which may individually or collectively assume any number of states. More specifically, the processor 1302 may operate as a finite-state machine, in response to executable instructions contained within the software modules disclosed herein. These computer-executable instructions may transform the processor 1302 by specifying how the processor 1302 transitions between states, thereby transforming the transistors or other discrete hardware elements constituting the processor 1302.

Encoding the software modules presented herein also may transform the physical structure of the computer-readable storage media presented herein. The specific transformation of physical structure may depend on various factors, in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

In light of the above, it may be appreciated that many types of physical transformations take place in the architecture 1300 in order to store and execute the software components presented herein. It also may be appreciated that the architecture 1300 may include other types of computing devices, including wearable devices, handheld computers, embedded computer systems, smartphones, PDAs, and other types of computing devices known to those skilled in the art. It is also contemplated that the architecture 1300 may not include all of the components shown in FIG. 13, may include other components that are not explicitly shown in FIG. 13, or may utilize an architecture completely different from that shown in FIG. 13.

FIG. 14 is a simplified block diagram of an illustrative computer system 1400 such as a PC, client machine, or server with which the present automated translation of clinical trial documents may be implemented. Computer system 1400 includes a processor 1405, a system memory 1411, and a system bus 1414 that couples various system components including the system memory 1411 to the processor 1405. The system bus 1414 may be any of several types of bus structures including a memory bus or memory controller, a peripheral bus, or a local bus using any of a variety of bus architectures. The system memory 1411 includes read only memory (ROM) 1417 and random access memory (RAM) 1421. A basic input/output system (BIOS) 1425, containing the basic routines that help to transfer information between elements within the computer system 1400, such as during startup, is stored in ROM 1417. The computer system 1400 may further include a hard disk drive 1428 for reading from and writing to an internally disposed hard disk (not shown), a magnetic disk drive 1430 for reading from or writing to a removable magnetic disk 1433 (e.g., a floppy disk), and an optical disk drive 1438 for reading from or writing to a removable optical disk 1443 such as a CD (compact disc), DVD (digital versatile disc), or other optical media. The hard disk drive 1428, magnetic disk drive 1430, and optical disk drive 1438 are connected to the system bus 1414 by a hard disk drive interface 1446, a magnetic disk drive interface 1449, and an optical drive interface 1452, respectively. The drives and their associated computer-readable storage media provide non-volatile storage of computer-readable instructions, data structures, program modules, and other data for the computer system 1400. Although this illustrative example includes a hard disk, a removable magnetic disk 1433, and a removable optical disk 1443, other types of computer-readable storage media which can store data that is accessible by a computer such as magnetic cassettes, Flash memory cards, digital video disks, data cartridges, random access memories (RAMs), read only memories (ROMs), and the like may also be used in some applications of the present automated translation of clinical trial documents. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof, are intended to cover non-transitory embodiments, and does not include waves, signals, and/or other transitory and/or intangible communication media.

A number of program modules may be stored on the hard disk, magnetic disk 1433, optical disk 1443, ROM 1417, or RAM 1421, including an operating system 1455, one or more application programs 1457, other program modules 1460, and program data 1463. A user may enter commands and information into the computer system 1400 through input devices such as a keyboard 1466 and pointing device 1468 such as a mouse. Other input devices (not shown) may include a microphone, joystick, game pad, satellite dish, scanner, trackball, touchpad, touchscreen, touch-sensitive device, voice-command module or device, user motion or user gesture capture device, or the like. These and other input devices are often connected to the processor 1405 through a serial port interface 1471 that is coupled to the system bus 1414, but may be connected by other interfaces, such as a parallel port, game port, or universal serial bus (USB). A monitor 1473 or other type of display device is also connected to the system bus 1414 via an interface, such as a video adapter 1475. In addition to the monitor 1473, personal computers typically include other peripheral output devices (not shown), such as speakers and printers. The illustrative example shown in FIG. 14 also includes a host adapter 1478, a Small Computer System Interface (SCSI) bus 1483, and an external storage device 1476 connected to the SCSI bus 1483.

The computer system 1400 is operable in a networked environment using logical connections to one or more remote computers, such as a remote computer 1488. The remote computer 1488 may be selected as another personal computer, a server, a router, a network PC, a peer device, or other common network node, and typically includes many or all of the elements described above relative to the computer system 1400, although only a single representative remote memory/storage device 1490 is shown in FIG. 14. The logical connections depicted in FIG. 14 include a local area network (LAN) 1493 and a wide area network (WAN) 1495. Such networking environments are often deployed, for example, in offices, enterprise-wide computer networks, intranets, and the Internet.

When used in a LAN networking environment, the computer system 1400 is connected to the local area network 1493 through a network interface or adapter 1496. When used in a WAN networking environment, the computer system 1400 typically includes a broadband modem 1498, network gateway, or other means for establishing communications over the wide area network 1495, such as the Internet. The broadband modem 1498, which may be internal or external, is connected to the system bus 1414 via a serial port interface 1471. In a networked environment, program modules related to the computer system 1400, or portions thereof, may be stored in the remote memory storage device 1490. It is noted that the network connections shown in FIG. 14 are illustrative and other means of establishing a communications link between the computers may be used depending on the specific requirements of an application of the present automated translation of clinical trial documents.

The subject matter described above is provided by way of illustration only and is not to be construed as limiting. Various modifications and changes may be made to the subject matter described herein without following the example embodiments and applications illustrated and described, and without departing from the true spirit and scope of the present invention, which is set forth in the following claims.

What is claimed is:

1. A computer-implemented method comprising:

splitting sentences in a digitized text of a stored document into segments;

ordering words in the segmented sentences having reduced complexity relative to the sentences prior to splitting;

at least partially translating the segments to a target natural language by matching the ordered segments to segments in a database of documents previously translated from a source natural language, wherein content of the documents have similar subject matter as the new document;

producing a single representation of the sentences that share a common meaning by applying transformational grammar to the digitized text; and outputting a representation of the stored document that includes a semantic meaning in the target natural language.

2. The method of claim 1, wherein the step of splitting sentences determines tokens that identify key sentence structures.

3. The method of claim 1, wherein the step of splitting sentences maintains semantic content of the sentences before they are split.

4. The method of claim 1, further comprising steps of:

recognizing words in the digitized text that match entries in a named entity table; and classifying the recognized words into pre-defined classes.

5. The method of claim 4, wherein the named entity table comprises one or more of proper nouns, abbreviations, acronyms; and the pre-defined classes comprise expressions of one or more of subject matter, sponsor, patron, location, organization, date, address, and time.

6. The method of claim 1, further comprising a step of marking portions of the digitized text for exclusion from translation to the target natural language.

7. The method of claim 1, further comprising a step of masking confidential information in the digitized text.

8. The method of claim 1, wherein, in the step of partially translating, the matching uses fuzzy logic that is less than 100 percent accurate.

9. The method of claim 1, wherein the applying transformational grammar includes detecting and transforming the detected passive voice sentences into active voice sentences.

10. The method of claim 1, wherein the applying transformational grammar includes detecting and transforming the detected indirect sentence form into a direct sentence form.

11. The method of claim 1, wherein the applying transformational grammar includes re-ordering words in the sentences based on sentence structure requirements of the target natural language.

12. The method of claim 1, further comprising a step of providing a user interface (UI) to enable a human to manually adjust one or more of splitting sentences, named entity recognition, matching database segments, and applying transformational grammar.

13. The method of claim 12, further comprising a step of executing a supervised machine learning process that accepts the manual adjustments as input.

14. The method of claim 1, wherein the representation of the new document is provided to a neural machine translation engine.

15. The method of claim 1, wherein a user-defined glossary is used to translate the identified words that match the entries in the named entity table.

16. The method of claim 1, further comprising a step of identifying and tagging parts of speech in the segments.

17. A computer-implemented method comprising:

splitting the digitized text in a new document into segments by identifying sentence boundaries using a gazetteer list of abbreviations to identify sentence marking stops;

identifying, using named entity recognition, the digitized text that is excluded from translation to a target natural language;

searching, using fuzzy matching, a translation history from the source natural language to the target natural language, for the segments between and existing translations;

identifying and tagging parts of speech in the digitized text;

grammatically transforming the digitized text to provide a single representation of sentences that have a common meaning;

over an application programming interface (API):

transmitting the segments to an external translation engine for translation;

receiving a translation of the segments in the target natural language from the external translation engine;

correcting the translation for subject matter specific acronyms and/or subject matter specific terminology; and reconstructing the new document using the corrected translation in the target natural language.

18. The method of claim 17, further comprising a step of translating the new document using adjustable machine learning processes.

19. A non-transitory computer-readable storage media storing executable instructions which, when executed by a processor steps of:

generating digitized text by deconstructing elements of one or more new documents into a data structure;

optimizing translation of the one or more new documents from a source language to a target language by pre-processing the generated digitized text into tokens, wherein the pre-processing identifies (1) key sentence structures that express relationships within a semantic domain of one of a subject matter specific terminology, and (2) a token order for translation; and providing the pre-processed digitized text token by token in an identified order to a neural machine translation engine.

20. The non-transitory computer-readable storage media of claim 19, further comprising steps of:

receiving, from the neural machine translation engine, translated tokens in the target language;

processing the received translated tokens to correct ontology in the semantic domain of the one of subject matter specific terminology; and reconstructing the new documents using the translated tokens with the corrected semantic ontology in which the reconstructed new documents in the target language maintain characteristics of the original new documents in the source language, the characteristics including one of formatting or embedded images.

* * * * *